United States Patent [19]

Naglieri et al.

[11] 4,356,320

[45] Oct. 26, 1982

[54] PREPARATION OF CARBOXYLIC ACIDS

[75] Inventors: Anthony N. Naglieri, Pine Brook; Nabil Rizkalla, River Vale, both of N.J.

[73] Assignee: The Halcon SD Group, Inc., New York, N.Y.

[21] Appl. No.: 839,948

[22] Filed: Oct. 6, 1977

Related U.S. Application Data

[63] Continuation-in-part of Ser. No. 740,146, Nov. 8, 1976, abandoned.

[51] Int. Cl.$^3$ .............................................. C07C 51/12
[52] U.S. Cl. .................................. 562/519; 260/413; 562/406
[58] Field of Search .................. 260/532, 515 R, 413; 560/232; 562/519, 406

[56] References Cited

U.S. PATENT DOCUMENTS

| | | | |
|---|---|---|---|
| 2,650,245 | 8/1953 | Thomas et al. | 560/232 |
| 3,855,307 | 12/1974 | Rony et al. | 260/532 |
| 3,856,856 | 12/1974 | Nozaki | 560/232 |
| 4,133,963 | 1/1979 | Holmes | 562/519 |

*Primary Examiner*—Natalie Trousof
*Attorney, Agent, or Firm*—William C. Long; Riggs T. Stewart; Harold N. Wells

[57] ABSTRACT

A carboxylic acid, such as acetic acid, is prepared from a hydrocarbyl alcohol, such as methanol, in carbonylation processes comprising the use of an iodide, carbon monoxide and a nickel catalyst in the presence of a promoter comprising an organo-phosphorus compound wherein the phosphorus is trivalent.

5 Claims, No Drawings

PREPARATION OF CARBOXYLIC ACIDS

CROSS-REFERENCE TO RELATED APPLICATION

This is a continuation-in-part of application Ser. No. 740,146 filed Nov. 8, 1976, now abandoned.

This invention relates to the preparation of carboxylic acids, more particularly mono-carboxylic acids, and especially lower alkanoic acids, such as acetic acid, by carbonylation.

Acetic acid has been known as an industrial chemical for many years and large amounts are used in the manufacture of various products. Proposals for producing carboxylic acids by the action of carbon monoxide upon alcohols (carbonylation) have been described, for example in Reppe et al U.S. Pat. No. 2,729,651. However, such prior proposals involving carbonylation reactions have required the use of very high pressures. More recently, carbonylation at lower pressures has been proposed. French Pat. No. 1,573,130, for example, describes the carbonylation of methanol and mixtures of methanol with methyl acetate in the presence of compounds of Group VIII noble metals such as iridium, platinum, palladium, osmium and ruthenium and in the presence of bromine or iodine under more moderate pressures than those contemplated by Reppe et al. Similarly, South African Pat. No. 68/2174 produces acetic acid from the same reactants using a rhodium component with bromine or iodine. Schultz (U.S. Pat. Nos. 3,689,533 and 3,717,670) has disclosed a vapor-phase process for acetic acid production employing various catalysts comprising a rhodium component dispersed on a carrier. These later carbonylation disclosures, however, require the use of expensive noble metals. It is an object of the present invention to provide an improved process for the manufacture of carboxylic acids, especially lower alkanoic acids, such as acetic acid, which requires neither high pressures nor Group VIII noble metals.

In accordance with the invention, it has been surprisingly discovered that a hydrocarbyl alcohol can be carbonylated at relatively low pressures if the carbonylation is carried out in the presence of a nickel catalyst, in the present of a promoter comprising an organo-phosphorus compound wherein phosphorus is trivalent and in the presence of an iodide in an amount which is substantially greater than disclosed by Reppe et al, i.e., at least 10 mols of an iodide, calculated as I, per 100 mols of the alcohol. The surprising discovery has been made that this catalyst-promoter system when used with the indicated high iodide concentration makes possible carbonylation at relatively low pressures, especially carbon monoxide partial pressures, in contrast to the process is disclosed in Reppe et al U.S. Pat. No. 2,729,651 in which, while employing a nickel-containing catalyst, the patentees find it necessary to use pressures of at least 200 atmospheres in their examples.

Thus, in accordance with the invention, carbon monoxide is reacted with a hydrocarbyl alcohol such as a lower alkyl alcohol, to produce a carboxylic acid, such as a lower alkanoic acid, the carbonylation taking place in the presence of an iodide, e.g., a hydrocarbyl iodide, especially a lower alkyl iodide, such as methyl iodide in an amount of the order specified above. Thus, acetic acid, for example, can be effectively prepared in a representative case by subjecting methyl alcohol to carbonylation in the presence of at least 10 mols methyl iodide per 100 mols of methanol, the carbonylation being carried out in the presence of the catalyst promoter-system described above.

It will be understood that the iodine moiety does not have to be added to the system as a hydrocarbyl iodide but may be supplied as another organic iodide or as the hydroiodide or other inorganic iodide, e.g., a salt, such as the alkali metal or other metal salt, or even as elemental iodine. Following the reaction the organic components of the reaction mixture are readily separated from one another, as by fractional distillation.

In like manner, other lower alkanoic acids, such as propionic acid, butyric acid, and valeric acid, can be produced by carbonylating the corresponding acid, and valeric acid, can be produced by carbonylating the corresponding lower alkyl alcohol such as ethyl alcohol, propyl alcohol, and the like. Similarly, other alkanoic acids, such as those containing up to 12 carbon atoms, for example capric acid, caprylic acid, and lauric acid, and like higher carboxylic acids are produced by carbonylating the corresponding alcohol, e.g., alkyl alcohols containing up to 11 carbon atoms in the alkyl group, heptyl alcohol, nonyl alcohol, undecyl alcohol, phenol, and the like.

The above-described reactions can be expressed as follows:

$$CO + ROH \rightarrow RCOOH \qquad (1)$$

wherein R is a hydrocarbyl radical which may be saturated, e.g., alkyl of
1 to 11 carbon atoms, or monocyclic aryl, e.g., phenyl or aralkyl, e.g., benzyl. Preferably, R is lower alkyl,
i.e., an alkyl group of 1 to 4 carbon atoms, such as methyl, ethyl, n-propyl, i-propyl, n-butyl, sec-butyl, and t-butyl.

The hydrocarbyl radical may be substituted with substituents which are inert in the reactions of the invention.

The more volatile components such as alkyl iodide and unreacted alcohol and byproducts such as esters and ethers in the final product mixture can be readily removed, as by distillation, for recycling, and the net yield of product is substantially exclusively the desired carboxylic acid. In the case of liquid-phase reaction which is preferred, the organic compounds are easily separated from the metal-containing components, as by distillation. The reaction is suitably carried out in a reaction zone to which the carbon monoxide, the alcohol, the iodide and the nickel catalyst and the promoters are fed.

In carrying out the process of the invention, a wide range of temperatures, e.g., 25° to 350° C. are suitable but temperatures of 100° to 250° C. are preferably employed and the more preferred temperatures generally lie in the range of 125° to 225° C. Temperatures lower than those mentioned can be used but they tend to lead to reduced reaction rates, and higher temperatures may also be employed but there is no particular advantage in their use. The time of reaction is also not a parameter of the process and depends largely upon the temperature employed, but typical residence times, by way of example, will generally fall in the range of 0.1 to 20 hours. The reaction is carried out under super-atmospheric pressure but, as previously mentioned, it is a feature of the invention that excessively high pressures, which require special high-pressure equipment, are not necessary. In general, the reaction is effectively carried out by employing a carbon monoxide partial pressure which is preferably 15 to 1000 psi and most preferably 30 to 200 psi, although carbon monoxide partial pressures of 1 to 10,000 psi can also be employed. By establishing the partial pressure of carbon monoxide at the values specified, adequate amounts of this reactant are always present. The total pressure is, of course, that which will provide the desired carbon monoxide partial pressure and preferably it is that rendered to maintain the liquid phase and in this case the reaction can be advantageously carried out in an autoclave or similar apparatus. The final reaction mixture will normally contain volatile components such as hydrocarbyl iodide, unreacted alcohol and may contain the corresponding ester and/or ether along with the product acid and these volatile components, after separation from the acid, can be recycled to the reaction. At the end of the desired residence time the reaction mixture is separated into its several constituents, as by distillation. Preferably, the reaction product is introduced into a distillation zone which may be a fractional distillation column, or a series of columns, effective to separate the volatile components from the product acid and to separate the product acid from the less volatile catalyst and promoter components of the reaction mixture. The boiling points of the volatile components are sufficiently far apart that their separation by conventional distillation presents no particular problem. Likewise, the higher-boiling organic components can be readily distilled away from the metal catalyst components and any organic promoter which may be in the form of a relatively non-volatile complex. Nickel catalyst, as well as promoter, including the iodide component, can then be combined with fresh amounts of alcohol and carbon monoxide and reacted to produce additional quantities of acid.

The ratio of the iodide to the alcohol in the reaction system can vary over a wide range as long as it is at least 10 mole per hundred mols of alcohol but ordinarily more than 200 mols of iodide, expressed as I, per 100 mols of iodine are not used. Typically, there are used 10 to 50 mols of the iodine per 100 mols of alcohol, preferably 17 to 35 mols per 100 mols.

The process is advantageously carried out in the presence of a solvent or diluent, particularly when the reaction has a relatively low boiling point, as in the case of methanol. The presence of a higher-boiling solvent or diluent, which may be the product acid itself, e.g., acetic acid in the case of methanol, or which may be the corresponding ester, e.g., methyl acetate, again in the case of methanol, will make it possible to employ more moderate total pressure. Alternatively, the solvent or diluent may be any organic solvent which is inert in the environment of the process such as hydrocarbons, e.g., octane, benzene, toluene, and the like. The carboxylic acid, when used, should preferably correspond to the acid being produced. A solvent or diluent other than the product itself is suitably selected which has a boiling point sufficiently different from the desired product in the reaction mixture so that it can be readily separated, as will be apparent to persons skilled in the art.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. The presence of minor amounts of water such as may be found in the commercial forms of the reactants is, however, entirely acceptable. Hydrogen which may be present as an impurity is not objectionable and even may tend to stabilize the catalyst. Indeed, in order to obtain low CO partial pressures the CO fed may be diluted with hydrogen or any inert gas such as those above mentioned. It has been surprisingly found that the presence of hydrogen does not lead to the formation of reduction products. The diluent gas, e.g., hydrogen, may generally be used in an amount up to about 95%, if desired.

The nickel catalyst component can be employed in any convenient form, viz., in the zero valent state or in any higher valent form. For example, the nickel to be added may be the metal itself in finely divided form, or a compound, both organic or inorganic, which is effective to introduce the nickel into the reaction system. Thus, typical compounds include the carbonate, oxide, hydroxide, bromide, iodide, chloride, oxyhalide, hydride, lower alkoxide (methoxide) phenoxide or nickel carboxylates wherein the carboxylate ion is derived from an alkanoic acid of 1 to 20 carbon atoms such as acetates, butyrates, decanoates, laurates, benzoates, and the like. Similarly, complexes of nickel can be employed, for example, nickel carbonyls and metal alkyls as well as chelates, association compounds and enol salts. Examples of other complexes include bis-(triphenyl phosphine) nickel dicarbonyl, tricyclopentadienyl trinickel dicarbonyl, and tetrakis (triphenyl phosphite) nickel.

Included among the catalyst components listed above are complexes of nickel with organic promoter ligands derived from the organic promoters hereinafter described. Particularly preferred are the elemental form, compounds which are iodides, and organic salts, e.g., salts of the monocarboxylic acid corresponding to the acid being produced. It will be understood that the foregoing compounds and complexes are merely illustrative of suitable forms of the nickel catalyst and are not intending to be limiting.

The nickel catalyst component employed may contain impurities normally associated with the commercially available metal or metal compounds and need not be purified any further.

The organic promoter is an organo-phosphorus compound wherein the phosphorus is trivalent. The organo-phosphorus promoter is preferably a phosphine, e.g., a phosphine of the formula

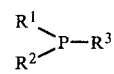

wherein $R^1$, $R^2$ and $R^3$ may be the same or different, and are alkyl, cycloalkyl, aryl groups, amide groups, e.g. hexamethyl phosphorus triamide, or halogen atoms, preferably containing up to 1 to 20 carbon atoms in the case of alkyl and cycloalkyl groups and 6 to 18 carbon atoms in the case of aryl groups. Typical hydrocarbyl phosphines include trimethylphosphine, tripropylphosphine, tricyclohexylphosphine and triphenylphosphine.

Although generally the organic promoter is added separately to the catalyst system, it is also possible to add it as a complex with the nickel such as bis-(triphenyl phosphine) nickel dicarbonyl, tricyclopentadienyl trinickel dicarbonyl, and tetrakis (triphenyl phosphite)

nickel. Both free organic promoters and complexed promoters can also be used. Indeed, when a complex of the organic promoter and nickel is used, free organic promoter can also be added as well.

The amount of nickel is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially, any amount of catalyst will facilitate the basic reaction and can be considered a catalytically-effective quantity. Typically, however, the nickel component of the catalyst is employed in the amount of 1 mol per 5 to 10,000 mols of alcohol, preferably 1 mol per 10 to 5,000 mols of alcohol, and most preferably 1 mol per 30 to 1,000 mols of alcohol.

The quantity of organic promoter can also vary widely but typically it is used in the amount of 1 mol per 1 to 10,000 mols of alcohol, preferably 1 mol per 10 to 5,000, most preferably 1 mol per 30 to 1,000 mols of alcohol.

As previously mentioned, in the working up of the reaction mixtures, e.g., by distillation, the promoter component can be readily recovered and recycled to the reaction. The nickel generally remains as the least volatile components, and is recycled. It may, however, distill with the volatile components, e.g., in the case of nickel carbonyl. The same is true of the promoter components.

It will be apparent that the above-described reactions lend themselves readily to continuous operation in which the reactants and catalyst, preferably in combination with the promoter, are continuously supplied to the appropriate reaction zone and the reaction mixture continuously distilled to separate the volatile organic constituents and to provide the desired product or products, e.g., carboxylic acid, with the other organic components being recycled and, in the case of liquid-phase reaction, a residual nickel-containing) and promoter-containing) fraction also being recycled. It has been observed that hydrogen, e.g., used as a CO diluent as indicated above, is of value in maintaining the catalyst at maximum activity on repeated recycle. During continuous operation, it will be apparent that the iodine moiety remains in the system at all times subject only to occasional handling losses or purges. The small amount of iodine makeup which may be needed from time to time is preferably effected by supplying the iodine in the form of the hydrocarbyl iodide but, as pointed out above, the iodine moiety may also be supplied as another organic iodide or as the hydrogen iodide or other inorganic iodide, e.g., a salt, such as the alkali metal or other metal salts, or as elemental iodine.

The following examples will serve to provide a fuller understanding of the invention, but it is to be understood that they are given for illustrative purposes only, and are not to be construed as limitative of the invention. In the examples all parts and percentages are on a molar basis, unless otherwise indicated. The various reactants and catalyst components are charged to the reaction vessel which is then closed and brought to the reaction temperature indicated.

EXAMPLE 1

Methanol (52 parts), methyl acetate (48 parts), methyl iodide (33 parts), water (11.8 parts), bis-triphenyl phosphine nickel dicarbonyl (2.1 parts) and triphenyl phosphine (1.6 parts) are charged at room temperature into a pressure vessel which is pressured to 400 psig carbon monoxide. The vessel is heated to 150° C. with stirring. The temperature is maintained at 150° C. and the pressure is kept at 725 psig by repressuring with carbon monoxide whenever needed. After 3 hours reaction time, G. C. analysis of the reaction effluent shows it to contain 35 mol % methyl acetate and 65 mol % acetic acid.

EXAMPLE 2

Methanol (76 parts), methyl acetate (24 parts), methyl iodide (33 parts), bis-triphenyl phosphine nickel dicarbonyl (2.1 parts) and triphenyl phosphine (0.8 part) are charged at room temperature into a pressure vessel which is pressured to 250 psig with carbon monoxide and then up to 400 psig with hydrogen. The vessel is stirred for one hour at 150° C. The pressure is maintained at 725 psig at the reaction temperature by charging carbon monoxide wherever needed. G. C. analysis of the reaction effluent shows it to contain 0.2% methanol, 1.4 mol % dimethyl ether, 35 mol % methyl acetate and 63.4 mol % acetic acid.

EXAMPLE 3

Methanol (76 parts), methyl acetate (24 parts), methyl iodide (16 parts), bis-triphenyl phosphine nickel dicarbonyl (1 part), and triphenyl phosphine (0.4 part) are charged at room temperature into a pressure vessel which is pressured to 250 psig with carbon monoxide and then up to 400 psig with hydrogen. The vessel was stirred for 1¾ hour at 175° C. The pressure is maintained at 950 psig at the reaction temperature by charging carbon monoxide whenever needed. G. C. analysis of the reaction effluent shows it to contain 4% methanol + dimethyl ether, 43% methyl acetate and 53% acetic acid.

EXAMPLE 4

Methanol (100 parts), bis-triphenyl phosphine nickel dicarbonyl (1 part), triphenyl phosphine (0.75 part), and methyl iodide (32 parts) are charged at room temperature to a pressure vessel and pressured with 300 psig carbon monoxide. The vessel is stirred for 5 hours at 150° C. G. C. analysis of the reaction effluent shows it to contain 42 mol % methanol + dimethyl ether, 45 mol % methyl acetate and 13 mol % acetic acid.

EXAMPLE 5

Methanol (100 parts), bis-triphenyl phosphine nickel dicarbonyl (2 parts), triphenyl phosphine (0.75 part), and methyl iodide (32 parts) are charged at room temperature to a pressure vessel and pressured with 300 psig of a carbon monoxide-hydrogen mixture (2:1 ratio). The vessel is stirred for 5 hours at 150° C. Analysis of the reaction effluent by gas chromatography (G. C.) at the end of the 5-hour reaction period shows it to contain 25.7 mol % dimethyl ether, 42 mol % methanol, 23 mol % methyl acetate and 9.3 mol % acetic acid.

EXAMPLE 6

Methanol (100 parts), nickel diacetate tetrahydrate (2 parts), triphenyl phosphine (5.7 parts), and methyl iodide (32 parts) were charged at room temperature to a pressure vessel which is then pressured with 400 psig carbon monoxide. The vessel is stirred for 62 hours at 150° C. G. C. analysis of the reaction effluent shows it to contain 1.6 mol % methanol + dimethyl ether, 23.2 mol % methyl acetate and 75.2 mol % acetic acid.

EXAMPLE 7

Methanol (100 parts), nickel iodide (2 parts), triphenyl phosphine (5.7 parts), and methyl iodide (32 parts) are charged at room temperature to a pressure vessel with 400 psig carbon monoxide. The vessel is stirred for 62 hours at 150° C. G. C. analysis of the reaction effluent shows it to contain 1.7 mol % methanol + dimethyl ether, 25.3 mol % methyl acetate and 73 mol % acetic acid.

What is claimed is:

1. A process for the preparation of a monocarboxylic acid which comprises reacting carbon monoxide and a hydrocarbyl alcohol in the presence of an iodide and in the presence of a catalyst consisting essentially of nickel or a nickel compound and a phosphine promoter, said iodide being employed in the amount of 10 to 200 mols, expressed as I, per 100 mols of alcohol, and said reacting being carried out at a temperature of 25°–350° C. and at a carbon monoxide partial pressure of 1–10,000 psi.

2. A process as defined in claim 1, wherein the acid is a lower alkanoic acid, and the hydrocarbyl alcohol is a lower alkyl alcohol.

3. A process as defined in claim 1, wherein the acid is acetic acid and the hydrocarbyl alcohol is methanol.

4. A process for the preparation of a monocarboxylic acid which comprises reacting carbon monoxide and a hydrocarbyl alcohol in the presence of an iodide and in the presence of a catalyst consisting essentially of nickel or a nickel compound and a phosphine promoter, said iodide being employed in the amount of 10 to 200 mols, expressed as I, per 100 mols of alcohol, and said reacting being carried out at a temperature of 25°–350° C. and at a carbon monoxide partial pressure of 15 to 1,000 psi.

5. A process for the preparation of a monocarboxylic acid which comprises reacting carbon monoxide and a hydrocarbyl alcohol in the presence of an iodide and in the presence of a catalyst consisting essentially of nickel or a nickel compound and a phosphine promoter, said iodide being employed in the amount of 10 to 200 mols, expressed as I, per 100 mols of alcohol, and said reacting being carried out at a temperature of 25°–350° C. and at a carbon monoxide partial pressure of 30–200 psi.

* * * * *

UNITED STATES PATENT AND TRADEMARK OFFICE
CERTIFICATE OF CORRECTION

PATENT NO. : 4,356,320

DATED : October 26, 1982

INVENTOR(S) : Anthony N. Naglieri et al

It is certified that error appears in the above-identified patent and that said Letters Patent is hereby corrected as shown below:

```
Col. 1, line 45 - "present" should be --presence--
Col. 1, line 55 - delete "is"
Col. 2, line 14 - delete "acid, and"
Col. 2, line 15 - delete entire line
Col. 2, line 16 - delete "corresponding"

Col. 4, line 41 - "intending" should be --intended--
Col. 4, line 63 - "tricyclohexylphosphineand" should be
                  --tricyclohexylphosphine and --
Col. 5, line 40 - delete ")" and change "and" to --(and--
Col. 6, line 20 - "wherever" should be --whenever--
```

Signed and Sealed this

Seventeenth Day of January 1984

[SEAL]

Attest:

GERALD J. MOSSINGHOFF

Attesting Officer

Commissioner of Patents and Trademarks